(12) United States Patent
Morishima et al.

(10) Patent No.: US 6,288,049 B1
(45) Date of Patent: Sep. 11, 2001

(54) FLUOROMETHOLONE OPHTHALMIC SUSPENSION

(75) Inventors: Kenji Morishima; Kazufumi Shiotani, both of Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/600,344
(22) PCT Filed: Jan. 19, 1999
(86) PCT No.: PCT/JP99/00138
§ 371 Date: Jul. 13, 2000
§ 102(e) Date: Jul. 13, 2000
(87) PCT Pub. No.: WO99/37286
PCT Pub. Date: Jul. 29, 1999

(30) Foreign Application Priority Data
Jan. 22, 1998 (JP) .................................................. 10-009987

(51) Int. Cl.$^7$ ................................................... A61K 31/56
(52) U.S. Cl. ............................................. 514/178; 514/912
(58) Field of Search .................................. 514/171, 178, 514/912

(56) References Cited

U.S. PATENT DOCUMENTS 5,149,693 * 9/1992 Cagle et al. ............................ 514/40

FOREIGN PATENT DOCUMENTS

| 59-130900 | 7/1984 | (JP) . |
| 1-213228 | 8/1989 | (JP) . |
| 8-295622 | 11/1996 | (JP) . |
| 10-36253 | 2/1998 | (JP) . |
| 11-29463 | 2/1999 | (JP) . |

* cited by examiner

Primary Examiner—Theodore J. Criares
Assistant Examiner—Jennifer Kim
(74) Attorney, Agent, or Firm—Frishauf, Holtz, Goodman, Langer & Chick, P.C.

(57) ABSTRACT

A fluorometholone ophthalmic suspension containing fluorometholone as an active ingredient, wherein a cellulosic polymer, such as hydroxypropylmethylcellulose or methylcellulose, and a nonionic surfactant, such as polysorbate 80, are added thereto to increase the redispersibility of the fluorometholone. The amount of the cellulosic polymer is preferably 0.0001 to 0.003 (W/V) %, and the amount of the nonionic surfactant is preferably 0.0001 to 0.5 (W/V) %. The fluorometholone ophthalmic suspension has excellent redispersibility and hardly forms aggregates.

20 Claims, No Drawings

FLUOROMETHOLONE OPHTHALMIC SUSPENSION

This application is a United States national phase of International Application PCT/JP99/00138, filed Jan. 19, 1999.

TECHNICAL FIELD

The present invention relates to improved compositions of an ophthalmic suspension containing fluorometholone, which is an anti-inflammatory synthetic adrenocorticosteroid, as an active ingredient.

BACKGROUND ART

Fluorometholone is a drug to be used for medical treatment as an anti-inflammatory steroid and is particularly widely used in the form of eye drops. Since fluorometholone is a drug which is hardly soluble in water, it is practically used in the form of ophthalmic suspensions. Since drugs are not dissolved in ophthalmic suspensions, it is necessary to shake the eye drop bottle in order to redisperse uniformly the settling and aggregating drug when the ophthalmic suspensions are used. Accordingly, a method of facilitating the redispersion is used wherein a nonionic surfactant such as polysorbate 80 is added to the ophthalmic suspensions.

The ophthalmic suspensions of fluorometholone are designed to improve redispersibility of the drug as mentioned above, but it is desirable to improve further the ophthalmic suspensions so that the redispersibility is much elevated and the drug can readily be dispersed uniformly. In the ophthalmic suspensions, it is also likely that the drug having been in a uniform dispersion state in preparation forms aggregates during preservation and the drug does not completely return to the original uniform dispersion state although the eye drops are shaken (irreversible aggregate formation). Accordingly, it is also desirable to improve the ophthalmic suspensions so as to reduce this aggregate formation.

SUMMARY OF THE INVENTION

As a result of precise studies to solve these problems, it was found that fluorometholone ophthalmic suspensions which are more excellent in redispersibility and hardly form aggregates are obtained by adding a nonionic surfactant and a cellulosic polymer. The nonionic surfactant works to improve the redispersibility of a drug, but it was difficult to prevent the drug sufficiently from forming aggregates with only the nonionic surfactant. As a result of studies of additives which reduce the aggregate formation of the drug, the cellulosic polymer was found to be appropriate. The cellulosic polymer exists among settled and concentrated drug particles and lowers contact frequencies of the particles, and thereby reducing the drug aggregation. However, adding only the cellulosic polymer causes problems that bubbles attached to the eye drop bottle are hard to remove and the redispersibility of the drug is lowered. The inventors found that it is possible to compensate for disadvantages of the nonionic surfactant and the cellulosic polymer and to develop advantages thereof by using these two in combination, and completed the present invention.

Studying also appropriate amounts of the nonionic surfactant and the cellulosic polymer, it was found that the amount of the nonionic surfactant is preferably 0.0001 to 0.5%, more preferably 0.001 to 0.1%, and the amount of the cellulosic polymer is preferably 0.0001 to 0.003%, more preferably 0.0005 to 0.002%. All percentages in the present invention mean W/V (%).

In general, the fluorometholone ophthalmic suspensions are used for medical treatment at a concentration of 0.02 to 0.1%. Accordingly, conducting the present invention, it is also preferable to prepare suspensions at this concentration, but the concentration is not limited to this range. The ophthalmic suspension of the present invention can be produced according to procedure of commercially available fluorometholone ophthalmic suspensions. Examples of the nonionic surfactant to be used in the present invention are polysorbate 80, polyoxyethylene hydrogenated castor oil, polyoxyethylene castor oil, polyoxyl 40 stearate and the like. Examples of the cellulosic polymer are hydroxypropylmethylcellulose, methylcellulose, hydroxypropylethylcellulose and the like. Additives widely used for an ophthalmic formulation, namely, a preservative such as benzalkonium chloride, an tonicity agent such as sodium chloride, a stabilizing agent such as disodium edetate, a buffer such as sodium hydrogenphosphate and the like, may be added to the ophthalmic suspension of the present invention besides the essential components, if necessary. The pH of the ophthalmic suspension can be preferably between 4 and 8, but it is not limited if pH is in a range widely used for an ophthalmic formulation.

BEST MODE FOR CARRYING OUT THE INVENTION

Example 1

(Study on effects of the invention)
1. Effects of addition of hydroxypropylmethylcellulose and polysorbate 80 on redispersibility and aggregation in a fluorometholone suspension (study (1))

(Preparation of suspensions)

Suspensions were prepared according to formulations shown in Table 1.

To simplify the explanation, only components which are essential in comparing and judging effects of the present invention are shown in the formulations. Benzalkonium chloride, sodium hydrogenphosphate, sodium dihydrogenphosphate, sodium chloride and disodium edetate were added as other additives.

TABLE 1

| | Amount (%) | | | |
| --- | --- | --- | --- | --- |
| Component | Control formulation 1 | Control formulation 2 | Formulation 1 | Formulation 2 |
| Fluorometholone | 0.1 | 0.1 | 0.1 | 0.1 |
| Hydroxypropylmethylcellulose | — | 0.001 | 0.001 | 0.001 |
| Polysorbate 80 | 0.03 | — | 0.001 | 0.005 |

Hydroxypropylmethylcellulose manufactured by Shin-etsu Chemical Industry Co., Ltd. was used.

Each suspension was prepared according to the following method.

First, in the above-mentioned formulation, a concentrated suspension (1%) containing excess fluorometholone was prepared by stirring with a stirrer for about one hour, and further stirred with a high-speed rotary mixer for about 30 minutes. The concentrated suspension was diluted with a vehicle (i.e. formulation except fluorometholone) so that a fluorometholone concentration became a prescribed concentration (0.1%). The suspension was filtrated with a 75 μm-mesh metallic screen to prepare each suspension.

(Method of judging effects)

Each suspension prepared according to the method mentioned above was charged into 5 ml eye drop bottles, and the bottles were preserved upright at 5° C. (10 bottles), 40° C. (10 bottles) or 60° C. (20 bottles) for two weeks and then left at room temperature for one day. Redispersibility and aggregate formation in each formulation were macroscopically inspected.

Another twenty bottles were preserved upright for eight days while altering the preservation temperature at 5° C. and 40° C. every other day (expressed as "Preserved alternately at 5° C. or 40° C.") and then left at room temperature for one day. These bottles were also inspected.

The inspection was carried out according to the following method.

Each eye drop bottle was slowly rotated, and the number of rotations required to completely redisperse a settled layer of the drug in a bottom of the eye drop bottle was counted (index of redispersibility).

The slow rotation was further continued, and the number of drug aggregates in a disperse phase was counted when the total number of rotations became 200. The drug aggregate means those which can macroscopically be observed as a mass.

(Results)

Results are shown in Tables 2 to 5. All the results are represented by the mean of the samples shown in the method of judging effects.

TABLE 2

(Preserved at 5° C.)

| | Number of rotations required for redispersion | Number of aggregates |
|---|---|---|
| Control formulation 1 | 41 | 6 |
| Control formulation 2 | 96 | 0 |
| Formulation 1 | 13 | 0 |
| Formulation 2 | 17 | 1 |

TABLE 3

(Preserved at 40° C.)

| | Number of rotations required for redispersion | Number of aggregates |
|---|---|---|
| Control formulation 1 | 42 | 2 |
| Control formulation 2 | 80 | 1 |
| Formulation 1 | 19 | 0 |
| Formulation 2 | 20 | 1 |

TABLE 4

(Preserved at 60° C.-1)

| | Number of rotations required for redispersion | Number of aggregates |
|---|---|---|
| Control formulation 1 | 33 | 3 |
| Control formulation 2 | 197 | 1 |

TABLE 4-continued (Preserved at 60° C.-1)

| | Number of rotations required for redispersion | Number of aggregates |
|---|---|---|
| Formulation 1 | 18 | 2 |
| Formulation 2 | 20 | 1 |

TABLE 5

(Preserved alternately 5° C. or 40° C.)

| | Number of rotations required for redispersion | Number of aggregates |
|---|---|---|
| Control formulation 1 | 30 | 17 |
| Control formulation 2 | 89 | 3 |
| Formulation 1 | 17 | 1 |
| Formulation 2 | 20 | 1 |

As apparent from the results shown in the above Tables, in the formulations 1 and 2 of the present invention, the numbers of rotations required for the redispersion are significantly smaller and the numbers of the aggregates are also improved, compared with the control formulation 1. Compared with the control formulation 2 wherein polysorbate 80, which is a nonionic surfactant, is not added, there is no difference with regard to the numbers of the aggregates, but the numbers of rotations required for the redispersion are much smaller. Thus addition effects of polysorbate 80, which is the nonionic surfactant, and hydroxypropylmethylcellulose, which is a cellulosic polymer, are remarkable.

2. Effects of addition of hydroxypropylmethylcellulose and polysorbate 80 on redispersibility and aggregation of a fluorometholone suspension (study (2))

In order to study more appropriate ranges of amounts of components, studies were carried out using suspensions of formulations shown in Tables 6 and 7 in the same manner as study (1).

TABLE 6

| | Amount (%) | |
|---|---|---|
| Component | Control formulation 3 | Control formulation 4 |
| Fluorometholone | 0.1 | 0.1 |
| Hydroxypropylmethylcellulose | — | — |
| Polysorbate 80 | 0.03 | 0.005 |

TABLE 7

| | Amount (%) | | | | | | | |
|---|---|---|---|---|---|---|---|---|
| Component | Formulation 3 | Formulation 4 | Formulation 5 | Formulation 6 | Formulation 7 | Formulation 8 | Formulation 9 | Formulation 10 |
| Fluorometholone | 0.1 | 0.1 | 0.1 | 0.1 | 0.1 | 0.1 | 0.1 | 0.1 |
| HPMC | 0.0001 | 0.0005 | 0.005 | 0.01 | 0.001 | 0.002 | 0.003 | 0.004 |
| Tween 80 | 0.005 | 0.005 | 0.005 | 0.005 | 0.005 | 0.005 | 0.005 | 0.005 |

HPMC: Hydroxypropylmethylcellulose
Tween 80: Polysorbate 80

(Results)

Results are shown in Tables 8 and 9. All the results are represented by the mean of the samples shown in the method of judging effects.

TABLE 8

(Preserved at 60° C.-2)

| | Number of rotations required for redispersion | Number of aggregates |
|---|---|---|
| Control formulation 3 | 27 | 52 |
| Control formulation 4 | 26 | 34 |
| Formulation 3 | 11 | 20 |
| Formulation 4 | 11 | 0 |
| Formulation 5 | 102 | 6 |
| Formulation 6 | 123 | 12 |

TABLE 9

(Preserved at 60° C.-3)

| | Number of rotations required for redispersion | Number of aggregates |
|---|---|---|
| Control formulation 3 | 31 | 75 |
| Control formulation 4 | 19 | 0 |
| Formulation 3 | 21 | 1 |
| Formulation 4 | 30 | 1 |
| Formulation 5 | 63 | 1 |
| Formulation 6 | 64 | 1 |

As apparent from the results shown in Tables 8 and 9, in the formulations wherein polysorbate 80, which is the nonionic surfactant, is added in the amount of 0.005%, when hydroxymethylcellulose, which is a cellulosic polymer, is added in the range of 0.0001 to 0.003%, the numbers of rotations required for the redispersion are remarkably small and the numbers of the aggregates are also improved. In particular, when hydroxymethylcellulose is added in the range of 0.0005 to 0.002%, the improvement of the numbers of the aggregates are remarkably excellent.

3. Effects of addition of methylcellulose and polysorbate 80 on redispersibility and aggregation of a fluorometholone suspension (Preparation of suspension)

Suspensions of the formulation shown in Table 10 were prepared. To simplify the explanation, only components which are essential in comparing and judging effects of the present invention are shown in the formulations. Benzalkonium chloride, sodium hydrogenphosphate, sodium dihydrogenphosphate, sodium chloride and disodium edetate were added as other additives.

TABLE 10

| | Amount (%) | | | |
|---|---|---|---|---|
| Component | Control formulation 1 | Control formulation 5 | Formulation 11 | Formulation 12 |
| Fluorometholone | 0.1 | 0.1 | 0.1 | 0.1 |
| Methylcellulose | — | 0.002 | 0.002 | 0.002 |
| Polysorbate 80 | 0.03 | — | 0.005 | 0.03 |

Methylcellulose manufactured by Shin-etsu Chemical Industry Co., Ltd. was used. The suspensions were prepared and their effects were judged in the same manner as study (1) except a preservation condition was employed. The preservation condition in the present study was as follows. Bottles were preserved upright for one week while altering the preservation temperature at 5° C. and 50° C. every other day (expressed as "Preserved alternately at 5° C. or 50° C.") and then left at room temperature for one day (10 samples).

(Results)

Results are shown in Table 11. All the results are represented by the mean of the samples shown above.

TABLE 11

(Preserved alternately at 5° C. or 50° C.)

| | Number of rotations required for redispersion | Number of aggregates |
|---|---|---|
| Control formulation 1 | 31 | 6 |
| Control formulation 5 | 194 | 1 |
| Formulation 11 | 29 | 3 |
| Formulation 12 | 24 | 3 |

As apparent from the results shown in the above Table, in the formulations 11 and 12 of the present invention, there is no difference with regard to the numbers of rotations required for the redispersion but the numbers of the aggregates are significantly smaller, compared with the control formulation 1. The numbers of rotations required for the redispersion are much smaller, compared with the control formulation 5 wherein polysorbate 80, which is the nonionic surfactant, is not added. Thus addition effects of polysorbate 80, which is the nonionic surfactant, and methylcellulose, which is a cellulosic polymer, are apparent.

Example 2

(Preparation example)

The following preparations were obtained according to the procedure described in Example 1. In the following preparation examples, amounts of respective components are represented by contents in 1 ml.

Preparation 1

| Component | Content |
|---|---|
| Fluorometholone | 1 mg |
| Hydroxypropylmethylcellulose | 0.01 mg |
| Polysorbate 80 | 0.01 mg |
| Benzalkonium chloride | 0.05 mg |
| Disodium edetate | 0.1 mg |
| Sodium hydrogenphosphate | 6 mg |
| Sodium dihydrogenphosphate | 0.6 mg |
| Sodium chloride | q.s. |
| Sterile purified water | q.s. |

A preparation similar to Preparation 1 can be obtained by changing the amount of hydroxypropylmethylcellulose to 0.001, 0.005, 0.02, 0.05 or 0.1 mg and changing the amount of polysorbate 80 to 0.005, 0.02, 0.05, 0.1, 0.3 or 0.5 mg in the above formulation.

Preparation 2

| Component | Content |
|---|---|
| Fluorometholone | 1 mg |
| Methylcellulose | 0.02 mg |
| Polysorbate 80 | 0.1 mg |
| Benzalkonium chloride | 0.05 mg |
| Disodium edetate | 0.1 mg |

-continued

| Component | Content |
|---|---|
| Sodium hydrogenphosphate | 6 mg |
| Sodium dihydrogenphosphate | 0.6 mg |
| Sodium chloride | q.s. |
| Sterile purified water | q.s. |

A preparation similar to Preparation 2 can be obtained by changing the amount of methylcellulose to 0.001, 0.005, 0.01, 0.05 or 0.1 mg and changing the amount of polysorbate 80 to 0.005, 0.01, 0.05, 0.3 or 0.5 mg in the above formulation.

The present invention relates to improved compositions of an ophthalmic suspension containing fluorometholone, which is widely used as an anti-inflammatory steroid, as an active ingredient and provides the improved compositions which are particularly excellent in redispersibility by adding a nonionic surfactant and a cellulosic polymer.

INDUSTRIAL APPLICABILITY

The present invention relates to improved compositions of an ophthalmic suspension containing fluorometholone, which is an anti-inflammatory synthetic adrenocorticosteroid, as an active ingredient and provides fluorometholone ophthalmic suspensions which are more excellent in redispersibility and hardly form aggregates.

What is claimed is:

1. A fluorometholone ophthalmic suspension consisting essentially of (i) an active ingredient consisting essentially of fluorometholone, (ii) a cellulosic polymer and (iii) a nonionic surfactant, wherein the cellulosic polymer and the nonionic surfactant are in amounts sufficient to increase the redispersibility of the fluorometholone, the suspension optionally further containing at least one additive selected from the group consisting of a preservative, a tonicity agent, a stabilizing agent and a buffer.

2. The ophthalmic suspension as claimed in claim 1, wherein the concentration of the cellulosic polymer is 0.0001 to 0.003 (W/V) % and the concentration of the nonionic surfactant is 0.0001 to 0.5 (W/V) %.

3. The ophthalmic suspension as claimed in claim 1, wherein the cellulosic polymer is hydroxypropylmethylcellulose.

4. The ophthalmic suspension as claimed in claim 1, wherein the cellulosic polymer is methylcellulose.

5. The ophthalmic suspension as claimed in claim 1, wherein the nonionic surfactant is polysorbate 80.

6. A fluorometholone ophthalmic suspension consisting essentially of (i) an active ingredient consisting essentially of fluorometholone, (ii) 0.0001–0.003 (W/V) % of hydroxypropylmethylcellulose and (iii) 0.0001–0.5 (w/V) % of polysorbate 80, wherein the hydroxypropylmethylcellulose and the polysorbate 80 increase the redispersibility of the fluorometholone, the suspension optionally further containing at least one additive selected from the group consisting of a preservative, a tonicity agent, a stabilizing agent and a buffer.

7. The ophthalmic suspension as claimed in claim 1, wherein the cellulosic polymer is in a concentration of 0.0005 to 0.002 (W/V) %.

8. The ophthalmic suspension as claimed in claim 1, wherein the nonionic surfactant is in a concentration of 0.001 to 0.1 (W/V) %.

9. The ophthalmic suspension as claimed in claim 1, wherein the fluorometholone is in a concentration of 0.02 to 1 (W/V) %.

10. The ophthalmic suspension as claimed in claim 1, wherein the nonionic surfactant is selected from the group consisting of polysorbate 80, polyoxyethylene hydrogenated castor oil, polyoxyethylene castor oil and polyoxyl 40 stearate.

11. The ophthalmic suspension as claimed in claim 10, wherein the cellulosic polymer is selected from the group consisting of hydroxypropylmethylcellulose and methylcellulose.

12. The ophthalmic suspension as claimed in claim 1, which further contains at least one additive selected from the group consisting of a preservative, a tonicity agent, a stabilizing agent and a buffer.

13. The ophthalmic suspension as claimed in claim 1, which further contains at least one additive selected from the group consisting of benzalkonium chloride, sodium chloride, disodium edetate and sodium hydrogenphosphate.

14. The ophthalmic suspension as claimed in claim 1, wherein the suspension has a pH of 4 to 8.

15. The ophthalmic suspension as claimed in claim 11, wherein the cellulosic polymer is in a concentration of 0.0005 to 0.002 (W/V) %; the nonionic surfactant is in a concentration of 0.001 to 0.1 (W/V) %; and the fluorometholone is in a concentration of 0.02 to 1 (W/V) %.

16. The ophthalmic suspension as claimed in claim 3, wherein the hydroxypropylmethylcellulose is in a concentration of 0.0005 to 0.002 (W/V) %.

17. The ophthalmic suspension as claimed in claim 16, wherein the fluorometholone is in a concentration of 0.02 to 1 (W/V) %.

18. The ophthalmic suspension as claimed in claim 6, wherein the fluorometholone is in a concentration of 0.02 to 1 (W/V) % and the suspension has a pH of 4 to 8.

19. The ophthalmic suspension as claimed in claim 18, wherein the hydroxypropylmethylcellulose is in a concentration of 0.0005 to 0.002 (W/V) % and the polysorbate 80 is in a concentration of 0.001 to 0.1 (W/V) %.

20. The ophthalmic suspension as claimed in claim 19, which further contains benzalkonium chloride, disodium edetate, sodium hydrogenphosphate, sodium dihydrogenphosphate, sodium chloride and sterile purified water.

* * * * *